(12) United States Patent
Meerdink et al.

(10) Patent No.: US 8,053,584 B2
(45) Date of Patent: Nov. 8, 2011

(54) PURIFICATION PROCESS FOR LACTIDE

(75) Inventors: Johannes Meerdink, Groningen (NL);
Nils Dan Anders Sädergard, Turku (FI)

(73) Assignee: Tate & Lyle Public Limited Company, London (GB)

( * ) Notice: Subject to any disclaimer, the term of this patent is extended or adjusted under 35 U.S.C. 154(b) by 807 days.

(21) Appl. No.: 10/582,280

(22) PCT Filed: Dec. 10, 2003

(86) PCT No.: PCT/NL03/00875
§ 371 (c)(1),
(2), (4) Date: Feb. 20, 2008

(87) PCT Pub. No.: WO2005/056509
PCT Pub. Date: Jun. 23, 2005

(65) Prior Publication Data
US 2008/0234500 A1    Sep. 25, 2008

(51) Int. Cl.
*C07D 313/00* (2006.01)
*B01D 3/00* (2006.01)
*C08G 63/82* (2006.01)

(52) U.S. Cl. .......... 549/274; 203/99; 528/354; 528/357; 528/361; 528/480; 528/481; 528/484; 528/485

(58) Field of Classification Search .......... 549/274; 528/354, 480, 481, 484, 485, 357, 361; 203/99
See application file for complete search history.

(56) References Cited

U.S. PATENT DOCUMENTS

| | | | |
|---|---|---|---|
| 5,023,350 A | 6/1991 | Bhatia | 549/274 |
| 5,117,008 A | 5/1992 | Bhatia et al. | 549/274 |
| 5,236,560 A | 8/1993 | Drysdale et al. | 203/99 |
| 5,521,278 A | 5/1996 | O'Brien et al. | 528/354 |

*Primary Examiner* — Andrew D Kosar
*Assistant Examiner* — Raymond Covington
(74) *Attorney, Agent, or Firm* — Williams, Morgan & Amerson, P.C.

(57) ABSTRACT

The present case relates to a process for the purification of lactide from a crude lactide vapor product stream which process comprises a rectification/condensation step leading to a lactide-enriched condensate.

21 Claims, 1 Drawing Sheet

Fig. 1

PURIFICATION PROCESS FOR LACTIDE

This invention relates to an improved process for the purification of lactide from a crude lactide vapour product stream comprising at least said lactide, lactic acid, water and linear lactic acid oligomers.

Lactides are dimeric cyclic esters of lactic acid and are intermediates in the preparation process of high molecular weight (HMW) polylactic acids (PLA), which are truly biodegradable polymers that can be utilised as substitutes for non-biodegradable polymers. The use of lactic acid and lactides for the manufacture of a biodegradable polymer is well known in e.g. the biomedical industry, where the polymer is used for making biodegradable sutures, clamps, bone plates and biologically active controlled release devices.

Lactide is most conveniently prepared by a two-step polymerisation/depolymerisation process. First, lactic acid from a feed source is polymerised to a relatively low molecular weight (oligomeric) polylactic acid (LMW-PLA). Second, the LMW-PLA is heated, generally in the presence of a catalyst, to depolymerise the LMW-PLA to lactide which is recovered as a component of a vapour product stream. Methods for performing the said polymerisation and depolymerisation are known in the art, see e.g. Gruter et al., U.S. Pat. No. 1,095,205 (1914); Lowe, U.S. Pat. No. 2,668,162 (1954); Bhatia, U.S. Pat. No. 4,835,293 (1989); DeVries, U.S. Pat. No. 4,797,468 (1989); and Muller, U.S. Pat. No. 5,053,522 (1991).

To obtain the high molecular weight polylactic acid (HMW-PLA) required for use as a biodegradable polymer it is essential that the lactides are obtained essentially free of other impurities, such as water, lactic acid, linear lactic acid oligomers and volatile derivatives of lactic acid, as in the presence of such impurities polylactic acid of insufficiently high molecular weight is obtained.

The vapour product stream that is produced by depolymerisation not only comprises lactide but also the above-mentioned impurities. In particular water and lactic acid are capable of participating in ring-opening reactions with the lactide, which results in a lower lactide yield and an increased acidity of the cyclic ester product.

Typically, purification of lactide may be achieved by solvent extraction or by recrystallisation from solvent. However, both methods are disadvantageous as they utilise solvents, which necessitates the need for facilities to store a solvent, to purify the product therefrom and to prevent the solvent from escaping into the environment. Hence, such steps add significantly to the process investment and operating costs. Moreover, recrystallisation is known to give relatively poor yields due to significant losses of lactide during the recrystallisation step. For the large-scale commercial production of biodegradable polylactic acid for an abundance of applications it is important to maximise yields and minimise costs to obtain a cost-competitive product.

Alternatively, distillation can be employed to purify lactide from a crude lactide vapour product stream (see e.g. EP 0 893 462 and EP 0 630 371, which are hereby incorporated herein by reference). The use of distillation for the purification of lactide allows for the continuous manufacture of cost-competitive HMW-PLA.

As an example, EP 0 630 371 discloses the use of fractional distillation for purification of lactides. Thereto, a crude lactide vapour stream that is produced by the depolymerisation of LMW-PLA in a reactor is completely or partially condensed and subsequently fed to a multi-stage distillation column. Three fractions are established in the column and removed therefrom: an overhead vapour fraction comprising lactic acid and water, a side vapour fraction comprising lactide and a bottom liquid fraction comprising lactide and linear lactic acid oligomers. The side vapour fraction comprising lactide may be condensed to yield a liquid lactide fraction. A purge stream of the bottom liquid fraction comprising lactide and linear lactic acid oligomers may be fed to the reactor such that the linear lactic acid oligomers may reparticipate in the depolymerisation reaction to optimise overall lactide yield. However, lactide with an acid content low enough to produce HMW-PLA was obtained only with very low yields.

EP 0 893 462 describes the use of distillation for purification of lactides. The crude lactide vapour stream may be fed to a conventional distillation column as such or may be completely or partially condensed prior to feeding to the column. Moreover, a distillation column is disclosed which is mounted directly on top of a reactor to create a single enclosed area within which both the reaction to generate the crude lactide vapour stream, and distillation thereof take place. It is disclosed that in the top-mounted distillation column equilibrium is established between low-boiling overhead components such as water and lactic acid, the intermediate-boiling component lactide and the high-boiling components, i.e. linear lactic acid oligomers; thus, a three-component separation is attempted. The high-boiling components, i.e. the linear lactic acid oligomers, that liquefy within the column travel down the distillation column directly into the reactor where they can be further reacted to form additional lactide. Thus, no purge stream is required between the distillation column and the reactor to obtain maximal LMW-PLA conversion and thus lactide yield. The low-boiling overhead stream composed essentially of water (or solvent) and lactic acid is removed, subsequently condensed and a portion is refluxed back into the distillation column. The desired product, i.e. the lactide, herein also referred to as the "lactide fraction" or "lactide containing fraction", is recovered via a side outlet. However, such top-mounted three-component separation system is very difficult to operate, particularly taking into account the fact that the system is located on top of a reactor, and it is difficult to envision that high yields of lactide with an acid content sufficiently low to produce HMW-PLA can thus be obtained.

In order to obviate one or more of the above drawbacks, the present invention provides an improved process for the purification of lactide with high yield and high purity, wherein the lactide is pre-purified in a rectification column separating the non-volatile components, i.e. linear lactic acid oligomers, and preferably a major part of the volatile components such as e.g. water and lactic acid, from the desired end-product lactide to increase the yield and purity of the lactide.

Thus, the present invention relates to a process for the purification of lactide from a crude lactide vapour product stream comprising at least said lactide, lactic acid, water and linear lactic acid oligomers, said crude lactide vapour product stream being produced by depolymerisation of low molecular weight polylactic acid in a reactor, which process comprises the steps of:

(a) feeding said vapour product stream to a rectification column having a feed inlet at the lower end of the column and an overhead vapour outlet at the upper end of the column, through the said feed inlet, said column being mounted onto the reactor such that components from the vapour product stream liquefying within the column are allowed to flow back into the reactor;

(b) establishing at the upper end of the column a first overhead vapour fraction consisting essentially of water, lactic acid and lactide, and at the lower end of the column a high-boiling fraction consisting essentially of lactide and higher-boiling linear lactic acid oligomers;

(c) condensing from said first overhead vapour fraction by means of a condenser at least the lactide to obtain a first liquid lactide containing condensate fraction;

(d) removing the first liquid lactide containing condensate fraction.

As known in the art, LMW-PLA and one or more catalysts can be fed to the reactor, where the crude lactide vapour product stream is produced by heating of the LMW-PLA in the presence of a catalyst. Suitable catalysts that may be present in the reactor are well known in the art and may comprise metals or inorganic/organic metal compounds such as Sn, Ti, Zn or Fe compounds.

Two optical isomers are known to exist for lactic acid, L-lactic acid and D-lactic acid. Either of the two lactic acid isomers or mixtures thereof may be used for the production of LMW-PLA and subsequent production of lactide to yield L-lactide, D-lactide and meso-lactide (DL-lactide) in any combination.

A typical depolymerisation reaction is conducted at a pressure of 10-100 mbar, preferably 20-50 mbar, at temperatures in the range of 160-270° C., preferably of 180-250° C., more preferably of 200-250° C. However, the depolymerisation can be conducted using any pressure and temperature. A skilled practitioner will readily be able to adjust these parameters.

Under the above conditions, the lactide produced by the depolymerisation of the LMW-PLA is removed by evaporation resulting in a crude lactide vapour product stream. In order to enhance the said removal, it is advantageous to apply a stream of an inert gas, such as e.g. nitrogen or argon gas in the reactor. The said crude lactide vapour product stream comprises at least lactide, lactic acid, water and linear lactic acid oligomers, such as linear lactic acid dimers, trimers, tetramers and higher oligomers, but may also comprise additional components, e.g. volatile lactic acid derivatives such as pyruvic acid. The composition of the crude lactide vapour product stream may depend on several parameters, such as for example the reaction temperature and pressure, the molecular weight of the introduced LMW-PLA and the type and amount of catalyst and/or initiator used. Typically, the lactide content in the crude lactide vapour product stream may be in the range of 65-99 wt. %, the lactic acid content may be in the range of 0-15 wt. % and the content of linear lactic acid oligomers may be in the range of 0-20 wt. % (see e.g. example 2 and 3). The crude lactide vapour product stream may additionally comprise by-products generated during the depolymerisation of LMW-PLA, such as e.g. pyruvic acid and acrylic acid, having an atmospheric boiling point of 165° C. and 140° C., respectively.

According to the invention, the crude lactide vapour product stream is directly fed to a rectification column. Entrance of the rectification column is therefore preferably not preceded by a condensation step. The term "rectification" is well known in the art and reflects the process of purification by means of fractionation based on volatility differences between components. The relative order of decreasing volatility of the principal components of the said stream is water, lactic acid, lactide and linear lactic acid dimers and higher oligomers with boiling points at atmospheric pressure of about 100, 215, 260 and 350° C., respectively, which boiling points are even higher for linear lactic acid trimers, tetramers, etc. The more volatile components in the said stream, such as water, lactic acid, lactide and volatile lactic acid derived species, such as for example acrylic acid and pyruvic acid, are evaporated more easily than the less volatile components, such as linear lactic acid dimers and higher oligomers, and thus travel higher in the column. As a consequence, a concentration gradient is established with the more volatile components being enriched at the upper end of the column and the less volatile components being enriched at the lower end of the column. Due to this concentration gradient a temperature gradient exists over the column. Thus, in the lower end of the column the temperature is highest and the concentration of the most volatile components, i.e. water, lactic acid and lactide, is lowest, and in the upper end of the column the temperature is lowest and the concentration of the most volatile components is highest.

Most efficient separation is achieved when at least a portion of the first liquid lactide containing condensate fraction of the more volatile components is refluxed, such that vapour and liquid fractions display a counter-flow within the column. Thus, an efficient separation is accomplished between components with a higher and components with a lower volatility. The person skilled in the art of rectification is aware of suitable conditions or is capable of establishing the said conditions in a straightforward manner in order to optimise the above separation.

As a concentration gradient of the compounds is present in the rectification column, outlets can be positioned in the column such, that fractions enriched in a desired product, e.g. lactide, can be removed from the column at the position of the said outlet. According to the present invention, the concentration gradient is established such, that the overhead vapour fraction at the upper end of the column is enriched in water, lactic acid and lactide, whereas the bottom vapour fraction at the lower end of the column is enriched in lactide and linear lactic acid oligomers. The lactide fraction is withdrawn at the upper end of the column.

According to the invention, said rectification column is mounted with its lower end onto the reactor such that a single enclosed area is provided wherein both the lactide production and purification take place. As a consequence, components liquefying in the rectification column are allowed to directly flow back into the reactor as to enable re-participation in the depolymerisation reaction. Thus, no purge stream as e.g. described in EP 0 630 371 is required to improve lactide yield. The rectification column can be any type of known rectification column allowing contact between the vapour and liquid fractions, such as e.g. a tray column or a packed column. Preferably, the rectification column is a packed column as packed columns are more conveniently used at reduced pressures. Preferably, the rectification column is packed with structured packing material in order to enhance contact between the vapour and liquid and to minimise the liquid hold-up. Minimising the liquid hold-up results in a lower pressure drop over the column. The skilled person is capable of applying the proper packing material for the envisaged aim. It is preferred that the rectification is conducted under reduced pressures.

The crude lactide vapour product stream produced in the reactor thus enters at the lower end of the rectification column at the feed inlet. The feed inlet is defined to be the column opening where the column is joined to the reactor. Herein, "lower end" defines a lower region in the column; lower end does therefore not necessarily mean the bottom of the column but may also be a location in the vicinity thereof.

At the upper end of the column, i.e. the end of the column that is not connected to the reactor, a first overhead vapour fraction is established consisting essentially of water, lactic acid and lactide, and at the lower end of the column a vapour fraction is established consisting essentially of lactide and higher-boiling linear lactic acid oligomers. One skilled in the art will be capable of determining and controlling appropriate pressures, temperatures and flows in the column to establish such fractions. Herein, "upper end" defines an upper region in the column; upper end does therefore not necessarily mean the top of the column but may also be a location in the vicinity thereof. However, preferably, the upper end of the column is at the top of the column.

From the first overhead vapour fraction in the upper end of the column at least the lactide is condensed by means of a condenser to obtain a first liquid lactide containing condensate fraction, and said first liquid lactide containing condensate fraction is removed from the column. Said first liquid lactide containing condensate, herein also referred to as rectified lactide, comprises lactide and may comprise water and lactic acid, but is preferably substantially void of linear lactic acid oligomers. Thus, the first liquid lactide containing condensate is essentially free of linear lactic acid oligomers and is therefore substantially purified in comparison to the crude lactide vapour product stream.

In a preferred embodiment step c) in the above process comprises partially condensing said first overhead vapour fraction, such that at least the water is left in the vapour phase and removed from the condenser, and at least the lactide is condensed to obtain a first liquid lactide containing condensate fraction. Thus, a more purified first liquid lactide containing condensate fraction is obtained mainly comprising lactide and possibly also lactic acid, but essentially void of both linear lactic acid oligomers and water. Preferably at least 80 wt. % of the water is removed in the vapour phase, more preferably at least 90 wt. %, even more preferably at least 95 wt. %, most preferably at least 98 wt. %. Therefore, the obtained first liquid lactide containing condensate fraction is substantially purified in comparison with the crude lactide vapour product stream, as the said condensate fraction comprises substantially less, or no water and less, or no linear lactic acid oligomers.

In a more preferred embodiment said step c) comprises partially condensing said first overhead vapour fraction, such that at least the water and a major amount of the lactic acid are left in the vapour phase and removed from the condenser, and at least the lactide is condensed to obtain a first liquid lactide containing condensate fraction, which results in an even more purified first liquid lactide containing condensate fraction comprising lactide and a minor amount of lactic acid, said fraction being essentially void of linear lactic acid oligomers, water and a major amount of lactic acid. Preferably at least 80 wt. % of the water is removed in the vapour phase, more preferably at least 90 wt. %, even more preferably at least 95 wt. %, most preferably at least 98 wt. %. Preferably at least 50 wt. % of the lactic acid is removed in the vapour phase, more preferably at least 60 wt. %, yet more preferably at least 70 wt. %, again more preferably at least 80 wt. %, most preferably at least 90 wt. %.

Condenser temperatures required for complete or partial condensation of lactide may vary. One skilled in the art will readily be able to determine suitable condenser temperatures. The (partial) condenser may be mounted on top of the rectification column or may be located downstream of the rectification column.

In order to efficiently remove the linear lactic acid oligomers from the crude lactide vapour product stream, a portion of the first liquid lactide containing condensate fraction is preferably refluxed into the column. The "reflux ratio" is a measure of how much of a liquid condensate is returned back to the column as reflux and is defined as the ratio of the liquid condensate flow refluxed into the column to the liquid condensate flow removed from the column. The reflux ratio is preferably between 0.01 and 5, more preferably between 0.025 and 2, most preferably between 0.05 and 1. A reflux ratio of 5 means e.g. that of the condensed matter 5 volumes are returned to the column whereas 1 volume is removed from the column.

Advantageously, the first liquid lactide containing condensate fraction comprises at least 90 wt. % lactide and 0-10 wt. % lactic acid, more preferably at least 96 wt. % lactide and 0-4 wt. % lactic acid.

Depending on the desired purity of the lactide, the first liquid lactide containing condensate fraction of step d) may be subjected to one or more distillation steps. Said distillation steps can be performed as is known e.g. from EP 0 623 153 and EP 0 893 462 or EP 0 630 371, but any type of distillation known in the art may be employed to further purify the first liquid lactide containing condensate fraction.

In a preferred embodiment, said one or more distillation steps comprise the steps of:

(i) feeding the first liquid lactide containing condensate fraction into a distillation column, the column having a bottom end and a top end and a feed inlet between said bottom end and top end, the column further comprising a second overhead vapour outlet at the top end of the column, a liquid outlet at the bottom end and a vapour side outlet located between the feed inlet and the liquid outlet;

(ii) establishing
   a second overhead vapour fraction comprising lactic acid and optionally water in the top end of the column,
   a bottom vapour fraction comprising lactide in the bottom end of the column, and
   a bottom liquid fraction below the bottom vapour fraction comprising lactide and linear lactic acid oligomers;

(iii) removing second overhead vapour fraction through the overhead vapour outlet;

(iv) removing bottom vapour fraction comprising lactide through the vapour side outlet;

(v) removing bottom liquid fraction through the liquid outlet.

For further purification the first liquid lactide containing condensate fraction is fed to a distillation column, herein also referred to as "second column". This second column comprises a feed inlet located between the top end and the bottom end of the column, whereto the first liquid lactide containing condensate fraction is fed. Preferably, the feed inlet is located at a distance of both the top end and the bottom and of the column, preferably near a midpoint of the column.

The distillation column may be any type of column known in the art allowing contact between the vapour and liquid fractions, such as e.g. a tray column or a packed column. Preferably, the distillation column is a packed column as such column is more conveniently used at reduced pressures. Preferably, the distillation column is packed with structured packing material as to enhance contact between the vapour and liquid and to minimise liquid hold-up, which results in a lower pressure drop over the column and in minimisation of reaction between the different species present. The skilled person is capable of applying the proper packing material for the envisaged aim.

In the process of distillation, as known in the art, a concentration gradient is established with the low-boiling components being enriched in the top end of the column, and the high-boiling components being enriched at the bottom end of the column. Thus, the second overhead vapour fraction is established in the top end of the column which is enriched in low-boiling components, i.e. lactic acid and optionally water. The liquid bottom fraction essentially comprises lactide and high-boiling linear lactic acid oligomers, the latter being formed due to side-reactions occurring under the operating conditions of the second column, whereas the bottom vapour fraction just above the bottom liquid fraction will consist essentially solely of lactide. Preferably, a reboiler is located at the bottom end of the column, generating the energy required for the purification.

The second overhead vapour fraction comprising lactic acid and optionally water is removed through the overhead vapour outlet and may subsequently be fed to a condenser to form a liquid lactic acid containing condensate fraction. Particularly when the second overhead vapour fraction still comprises water, the condenser can be a partial condenser to remove water to also generate a purified liquid lactic acid condensate fraction. Preferably, a portion of the generated liquid lactic acid containing condensate fraction is refluxed back into the second column in order to obtain efficient separation between lactic acid and lactide. The reflux ratio is preferably in the range of 0.1-20, more preferably in the range of 0.5-15, most preferably in the range of 1-10.

The bottom vapour fraction comprising lactide is removed through a vapour side outlet located between the bottom end and midpoint of the second column. Preferably, the vapour side outlet is located slightly above the boiling liquid bottom fraction, such that essentially solely lactide is removed through the said vapour side outlet.

Preferably, a portion of the bottom liquid fraction is removed from the second column to prevent accumulation of linear lactic acid oligomers in the liquid fraction.

The feed rate of the first liquid lactide containing condensate fraction to the column and the removal rates of the second overhead vapour fraction, the bottom vapour fraction and the bottom liquid fraction are preferably co-ordinated such that a substantially steady-state condition can be maintained in the column as to allow for a continuous process to occur. One skilled in the art will readily be able to establish suitable feed and removal rates.

In the distillation step, best results are achieved at low temperatures and pressures. Lower temperatures minimise the possible occurrence of side-reactions between lactic acid and lactide that can lead to product loss and contamination of the bottom vapour fraction comprising lactide. Preferably, the distillation step is carried out under reduced pressures, more preferably at pressures of 10-100 mbar, most preferably of 20-50 mbar, preferably at a temperature of no more than 180° C., more preferably of no more than 170° C., even more preferably of no more than 160° C., preferably of about 150° C. Moreover, it is preferred that the processes of depolymerisation of LMW-PLA, rectification and distillation are conducted in a continuous manner.

In a preferred embodiment said distillation step further comprises the step of (vi) condensing the bottom vapour fraction comprising lactide obtained in step (iv) to obtain a second liquid lactide containing condensate fraction. Condensation is preferred as lactide in liquid condensed form is more easily fed to any following system, e.g. an additional purification system or a polymerisation, system.

The bottom vapour fraction and/or the second liquid lactide containing condensate fraction that are obtained as described above preferably comprise at least 99 wt. %, preferably at least 99.5 wt. %, lactide. The amount of hydroxyl containing compounds in the bottom vapour fraction and/or second liquid lactide containing condensate fraction are preferably less than 50 meq/kg, more preferably less than 20 meq/kg and most preferably less than 10 meq/kg. Thus, a polymer grade lactide is obtained which is e.g. suitable for the production of HMW-PLA.

In another embodiment, the bottom liquid fraction of the distillation step is recycled to the reactor to optimise overall lactide yield from a feed source.

In a further aspect, the invention relates to a process as disclosed above, said process further comprising the step of removing carboxylic acid and/or hydroxyl containing compounds in any of the lactide comprising fractions obtained in step (d), (iv), (v) or (vi) to further purify the said lactide comprising fractions.

Said removal of residual acids can e.g. be accomplished by well-known processes in the state of the art, such as the addition of organic bases such as pyridine and trialkylamines or phosphines to the lactide comprising fraction to form salts with the acids, scavenging of acids with basic metal salts or by using activated charcoal or silica or alumina powders whereto the acids adsorb. However, any chemical process for the removal of carboxylic acid and/or hydroxyl containing compounds from any of the lactide comprising fractions can be used.

The lactide comprising fraction can be obtained in step (d), (iv), (v) or (vi) and comprises at least lactide and optionally lactic acid, water and linear lactic acid oligomers. However, other carboxylic acid and/or hydroxyl containing compounds may also be present. The lactide comprising fraction may be vaporous such as the lactide comprising fraction obtained in step (iv) or may be liquid such as the lactide comprising fraction obtained in either of the steps (d), (v) or (vi).

Preferably, said removing carboxylic acid and/or hydroxyl containing compounds in any of the lactide comprising fractions obtained in step (d), (iv), (v) or (vi) comprises the steps of:

I. contacting any of the lactide comprising fractions obtained in step (d), (iv), (v) or (vi) with a solid scavenger material comprising at least one functional moiety capable of forming a covalent bond with one or more carboxylic acid and/or hydroxyl containing compounds optionally present in said lactide comprising fraction, thereby allowing the at least one functional moiety of the scavenger material to selectively react with the one or more carboxylic acid and/or hydroxyl containing compounds optionally present in said lactide comprising fraction to form a bond therewith;

II. separating the scavenger material with bound carboxylic acid and/or hydroxyl containing compounds from the lactide comprising fraction to obtain a substantially purified lactide comprising fraction.

The latter scavenging process for removing carboxylic acid and/or hydroxyl containing compounds such as water, lactic acid and linear lactic acid oligomers from a lactide comprising fraction comprising at least lactide is advantageous, as it does not have the drawbacks conventional processes have. The removal of acids by addition of organic bases is generally not suitable at elevated temperatures, many nitrogen-containing bases show a tendency to oxidise and colour the acid containing mixture, and metal ion may act as catalysts, especially in mixtures containing polymerisable molecules, such as lactic acid containing mixtures. A major drawback of the charcoal and silica or alumina powders is the low capacity at low acid concentrations and at high temperatures.

The above irreversible scavenging process is suitable not only for removal of lactic acid and linear lactic acid oligomers from a lactide comprising fraction comprising at least lactic acid and lactide, but can be used for removal of any carboxylic acid and/or hydroxyl containing compound(s) from any mixture of compounds to obtain a substantially purified product.

Moreover, the said process can be used for removal of lactic acid and/or linear lactic acid oligomers from any lactide containing preparation.

The solid scavenger material can e.g. be in the form of a powder, beads, fibers, strand, woven or non-woven materials. Such materials can easily be separated from a liquid with any viscosity.

The scavenging process can be performed in any type of system that allows contacting the lactide comprising fraction, either in vapour or liquid form, with the solid scavenger material. Methods for contacting and separating the lactide comprising fraction and the solid scavenger material will be readily apparent to one skilled in the art. Said contacting could for example be accomplished by passing a vaporous lactide comprising fraction, such as the lactide comprising fraction obtained in step (iv), along a surface comprising the solid scavenger material, or simply by mixing a liquid lactide comprising fraction, such as the lactide comprising fraction obtained in step (d), (v) or (vi), with beads comprising the solid scavenger material. Separation of the lactide comprising fraction and the scavenger material can be accomplished by any conventional means such as e.g. filtration.

By choosing a specific functional moiety the acid scavenging process can be fine-tuned. E.g. isocyanates react relatively fast with hydroxyl groups, anhydrides are known to react relatively fast with alcohol groups, epoxidised groups are particularly suitable for removal of compounds with a carboxylic acid group, etc. Preferably, the at least one functional moiety of the scavenger material is selected from the group, consisting of epoxy, amine, amide, cyano and anhydride moieties. Non-limiting examples of such reactive moieties are resins based on olefinic copolymers containing maleic anhydride acryl amide or glycidylmethacrylate comonomers.

The scavenger process can be carried out in a batch or continuous way. Preferably, the acid scavenging is conducted in a continuous manner to provide an efficient and cost-effective process. Preferably, the acid scavenging is conducted at elevated temperatures, more preferably at temperatures in the range of 100-180° C., most preferably in the range of 100-150° C.

The invention will now be illustrated with reference to figures and examples.

Figure 1:
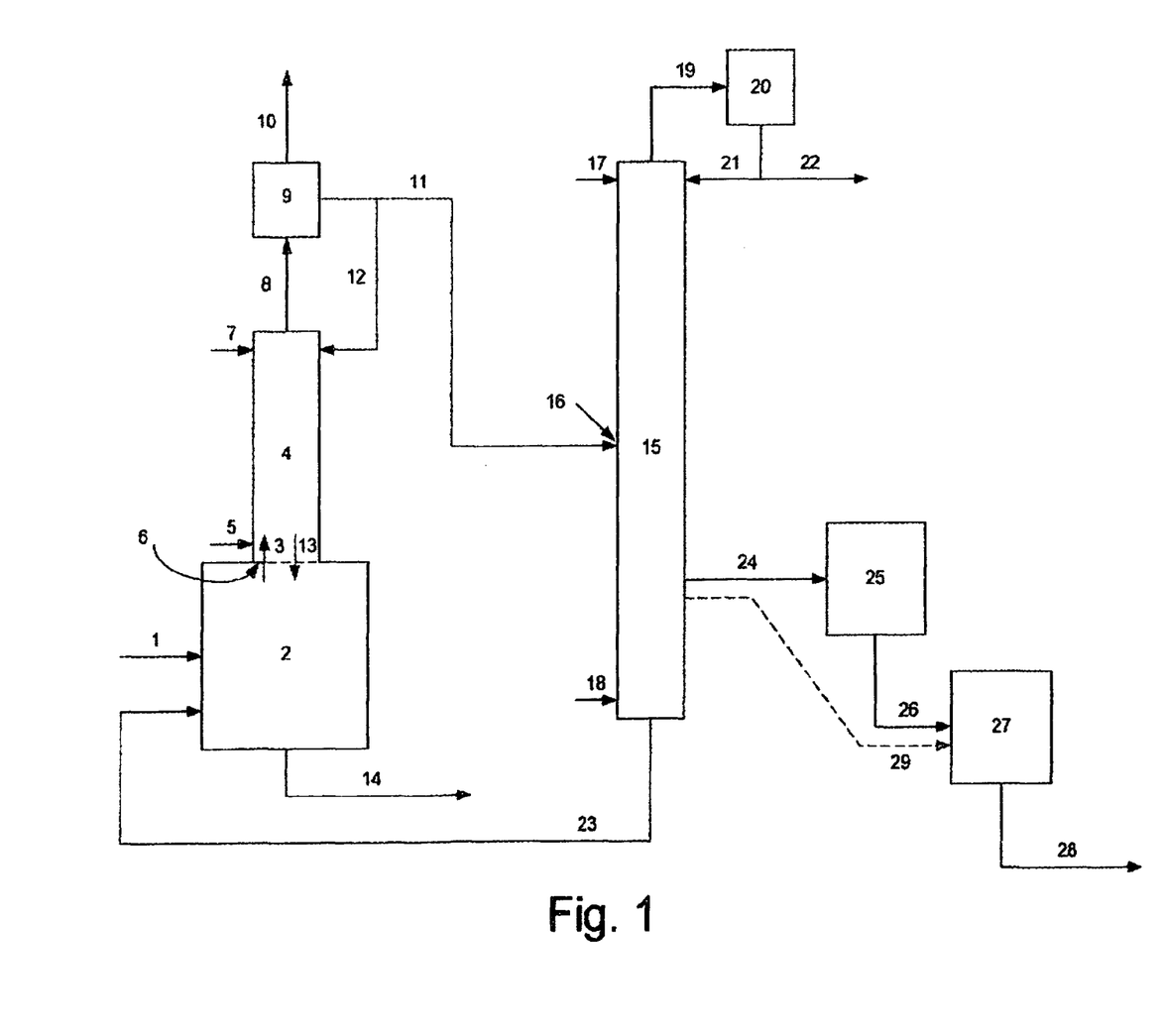

Referring now to FIG. 1, LMW-PLA is fed through line 1 to a reactor 2. In the reactor 2 lactide is produced by depolymerisation of the LMW-PLA at a temperature and pressure sufficient to vaporise the lactide as it is generated, resulting in a crude lactide vapour product stream (arrow 3). Reactor 2 may contain the required catalyst; alternatively, the catalyst can be fed to the reactor 2 by a separate line (not shown) or may be co-fed with the LMW-PLA via line 1.

The crude lactide vapour product stream 3 enters a rectification column 4 that is mounted onto the reactor 2 such that the reactor 2 and the column 4 form a single enclosed area. The crude lactide vapour product stream 3 enters the rectification column 4 at the lower end 5 of the column through feed inlet 6. In order to enhance removal of the produced lactide from the reactor 2 to the column 4, a stream of nitrogen or any other inert gas may be inserted into the reactor 2 (not shown). The more volatile components of the crude lactide vapour product stream 3 are being enriched at the upper end 7 of the column 4, whereas less volatile components are enriched at the lower end 5 of the column 4. As a consequence, in the upper end 7 of the column 4 a first overhead vapour fraction consisting essentially of water, lactic acid and lactide is established, and a high-boiling fraction consisting essentially of lactide and higher-boiling linear lactic acid oligomers is established at the lower end 5 of the column 4. The overhead vapour fraction is removed via line 8 and subsequently fed to a condenser or partial condenser 9 which may be located downstream of the rectification column 4 or may be mounted on top of the rectification column 4. In the (partial) condenser 9 at least the lactide is condensed to obtain a purified first liquid lactide containing condensate fraction. Preferably, the overhead vapour fraction is partially condensed such that water and preferably also a major amount of the lactic acid present are left in the vapour phase and are removed from the (partial) condenser 9 via line 10. The first liquid lactide containing condensate fraction is removed from the (partial) condenser 9 through line 11. A portion of the first liquid lactide containing condensate fraction may be refluxed to the rectification column 4 through line 12 in order to obtain efficient separation of the components in the crude lactide vapour product stream 3. It is preferred that the refluxed first lactide containing condensate fraction comprises no water as to prevent occurrence of side-reactions and to maximise lactide yield. As a result of the reflux, heat exchange may occur between more volatile liquid components, such as water, lactic acid or lactide, and the less volatile vapour components, such as linear lactic acid oligomers, whereby the more volatile components become vaporous whereas the less volatile components may liquefy. These liquefied components may travel down the column to re-enter the reactor 2 (arrow 13). In the reactor 2 the liquefied components may again participate in the depolymerisation reaction.

An optional purge stream 14 comprising LMW-PLA and linear lactic acid oligomers may be removed from the reactor 2, e.g. to maintain a good quality of the reactor content regarding crude lactide production.

The first liquid lactide containing condensate fraction may be used directly, but is preferably fed through line 11 to a distillation column 15 through a feed inlet 16 that is located between the top end 17 and the bottom end 18 of the column 15. In the distillation column 15 temperatures and pressures are operated such that an overhead vapour fraction comprising mainly lactic acid, a bottom vapour fraction comprising mainly lactide, and a bottom liquid fraction below the bottom vapour fraction, comprising mainly lactide and linear lactic acid oligomers, are established. To this end, preferably a reboiler is present, preferably at the bottom end 18 of the column 15 (not shown). The overhead vapour fraction comprising mainly lactic acid is removed from the distillation column 15 via line 19 and may subsequently be fed to a condenser 20 to form a liquid lactic acid containing condensate fraction. A portion of the liquid lactic acid containing condensate fraction may be refluxed back to the distillation column through line 21 to achieve optimal separation of components of the first liquid lactide containing condensate fraction as described above, and the other portion of the liquid lactic acid containing condensate fraction may be removed from the condenser 20 through line 22 and may be discarded or may be re-used as feed source to be polymerised to LMW-PLA. The bottom liquid fraction may be removed from the column 15 via line 23 and may be recycled to the reactor 2 to increase the overall lactide yield. The bottom vapour fraction comprising the purified lactide is removed through line 24 and may subsequently be fed to a condenser 25 to obtain a second liquid lactide containing condensate fraction, which may be fed to any further purification system, to any polymerisation system or which may be stored for further processing. Optionally, the second liquid lactide containing condensate fraction may be fed through line 26 to any type of system 27 wherein the lactide containing fraction is contacted with the solid scavenger material to further remove carboxylic acid and/or hydroxyl containing compounds.

Alternatively, the bottom vapour fraction comprising the purified lactide may be removed from the column 15 via line 29 and may be fed to any type of system 27 wherein the lactide containing fraction is contacted with solid scavenger material to further remove carboxylic acid and/or hydroxyl containing compounds.

From the system 27 the lactide comprising fraction can be recovered by separation of the lactide comprising fraction from the solid scavenger material, e.g. by simple filtration. The lactide comprising fraction may now be removed via line 28 and may be stored or fed to any following system.

The following examples are presented to further illustrate specific embodiments of the present invention and are not in any way to be interpreted as being limiting.

The water content was determined by Karl-Fischer titration. The free acid content was determined by potentiometric titration. Unless otherwise indicated, the molecular weight of polylactic acid was determined by GPC in comparison with polystyrene standard. Lactic acid, lactides and lactic acid species that include linear lactic acid oligomers and (volatile) by-products generated during the depolymerisation of LMW-PLA were determined by HPLC. Some of the samples were analysed by NMR. Analyses were performed according to standard procedures known in the art.

EXAMPLE 1

Molecular Weight Polylactic Acid Versus Lactic Acid impurities

The molecular weight of polylactic acid is controlled by the amount of hydroxylic impurities in lactide. Lactide with different concentrations of lactic acid and oligomers of lactic acid (meq/kg) was polymerised to polylactic acid to show the effect of these impurities on the molecular weight. The polymerisation was carried out at 180° C. with 0.1 wt. % stannous octoate as the catalyst under inert atmosphere.

| Lactic acid impurities (meq/kg) | Molecular weight (Mn, g/mol) |
|---|---|
| 10 | 111,200 |
| 13 | 79,300 |
| 18 | 48,600 |
| 43 | 23,300 |
| 60 | 15,300 |
| 121 | 13,200 |

EXAMPLE 2

Crude Lactide

Low molecular weight poly(L-lactic acid) (250-300 g) was placed in a specifically designed laboratory distillation set-up for the production of crude lactide. This set-up consists of a 3-neck flask (500 ml) with large magnetic stir bar and heated oil bath (210-230° C.), a vigreux column wrapped with a controlled heating tape (140-170° C.), insulation tape and 3-flask sample collection system at room temperature. A vacuum of 30 mbar was maintained for production and evaporation of the crude lactide. A distillation fraction of crude lactide was collected for 1-2 hours. The solidified crude lactide fraction was retained for analysis for free acid, water and composition. The composition of the analysed crude lactide is given in the table below, together with the molecular weight of the low molecular weight polylactic acid. As can been seen from the free acid content, and water content, a high molecular weight polylactic acid can not directly, without further purification, be obtained from crude lactide.

| | | Example | | | |
|---|---|---|---|---|---|
| | | 2-1 | 2-2 | 2-3 | 2-4 |
| Mn PLA | g/mol | 1120 | 1870 | 2050 | 1970 |
| Mw PLA | g/mol | 5440 | 5110 | 5230 | — |
| Catalyst | — | stannous octoate | stannous octoate | stannous octoate | zinc stearate |
| Amount of catalyst | wt. % | 0.2 | 0.2 | 0.2 | 0.1 |
| Crude lactide | | | | | |
| Free acid | meq/kg | 840 | 1940 | 1240 | 510 |
| Water | ppm | 1650 | | 6000 | |
| L-lactide (incl. D-lactide) | wt. % | 86.2 | 70.3 | 77.2 | 81.6 |
| Meso-lactide | wt. % | 3.9 | 4.5 | 5.8 | 9.1 |
| Lactic acid | wt. % | 2.7 | 9.9 | 7.9 | 3.7 |
| Lactic acid species | wt. % | 7.2 | 15.3 | 9.1 | 5.6 |

EXAMPLE 3

Crude Lactide

Crude lactide was continuously produced in a stirred tank reactor by feeding continuously low molecular weight poly (D,L-lactic acid). The produced vapour crude lactide entered a column with a partial condenser. The column was directly mounted on the reactor. At the top of the column, after the condenser, water, lactic acid and some lactide(s) were removed. At a lower point of the column the liquefied crude lactide fraction was removed. This fraction was analysed. The reaction mass, that was 26 kg, the temperature and the pressure were kept constant during the process. In the table given below the results of the continuously crude lactide production are given.

| | | Example | | | | |
|---|---|---|---|---|---|---|
| | | 3-1 | 3-2 | 3-3 | 3-4 | 3-5 |
| Mn PLA[a] | g/mol | 380 | 560 | 560 | 530 | 530 |
| Temperature | ° C. | 215 | 235 | 230 | 245 | 215 |
| Pressure | mbara | 22 | 50 | 50 | 60 | 60 |
| Catalyst | — | stannous oxide | none | stannous oxide | none | stannous oxide |
| Amount of catalyst | wt. % | 0.1 | | 0.1 | | 0.1 |
| Crude lactide rate | kg/h | 17 | 10.5 | 27 | 7.0 | 9.5 |
| Crude lactide | | | | | | |
| Water | ppm | 4600 | | | | |
| Lactide | wt. % | 78.3 | 76.6 | 82.9 | 81.3 | 89.7 |
| Lactic acid | wt. % | 10.9 | 4.6 | 2.7 | 12.6 | 6.0 |
| Lactic acid species | wt. % | 10.9 | 18.8 | 14.4 | 6.2 | 4.3 |

[a]Determined by NMR.

EXAMPLE 4

Continuous Production and Rectification of Crude Lactide Rectified Lactide

Vaporous crude lactide was continuously produced in a falling film evaporator by continuously feeding low molecular weight poly(L-lactic acid). The catalyst used was stannous octoate and its concentration in the reaction mixture was about 0.1 wt. %. The produced vaporous crude lactide was directly entered into a rectification column in which a separation was established between the higher boiling components in crude lactide, such as the linear dimer of lactic acid and higher oligomers of lactic acid and the lower boiling components in crude lactide, like water, lactic acid, lactide and volatile by-products, by refluxing a part of the top product back to the column. On top of the column a partial condensation was applied.

In this way three different fractions can be identified; (1) a liquid bottom fraction that contains lactide and the oligomers of lactic acid, (2) a vaporous top fraction that contains most of the water and some lactic acid and lactide, (3) a liquid top fraction, called rectified lactide, that contains mostly lactic acid and lactide. The operation pressure was 25 mbara and the reflux ratio was about 0.5. The top vapour temperature was about 141-142° C. and the partial condensed vapour temperature about 103-105° C. The liquid top fraction, called rectified lactide, was analysed for the free acid content and the different components like lactic acid, lactide(s), and lactic acid species. The term lactic acid species refers to the linear dimer and higher oligomers of lactic acid as well as (volatile) by-products formed during the depolymerisation of low molecular weight polylactic acid. Due to the volatility of the latter by-products, these were concentrated in the top of the column. The rectification column was packed with structured packing material in order to enhance contact between the vapour and the liquid and to minimize the liquid hold-up.

As can been seen from the free acid content, a high molecular weight polylactic acid cannot directly, without further purification, be obtained from the produced rectified lactide.

|  |  | Example | | |
|---|---|---|---|---|
|  | — | 4-1 | 4-2 | 4-5 |
| Mn PLA | g/mol | 1380 | 1100 | 1540 |
| Mw PLA | g/mol | 4170 | 3110 | 3420 |
| Reactor temperature | ° C. | 220 | 214 | 217 |
| Rectified lactide | kg/h | 65 | 67 | 65 |
| Free acid | meq/kg | 360 | 395 | 327 |
| L-lactide (incl. D-lactide) | wt. % | 83.9 | 83.7 | 88.3 |
| Meso-lactide | wt. % | 13.8 | 12.5 | 9.6 |
| Lactic acid | wt. % | 1.8 | 3.0 | 1.6 |
| Lactic acid species | wt. % | 0.5 | 0.7 | 0.6 |

EXAMPLE 5

Continuous Distillation of Rectified Lactide

Rectified lactide was continuously purified in a distillation column having a top stream and a bottom stream. In the top stream lactic acid and volatile lactic acid species were concentrated, in the bottom stream lactide was concentrated. The distillation column was packed with structured packing material in order to enhance contact between the vapour and the liquid and to minimise the liquid hold-up. The top pressure was 25 mbara and the reflux ratio applied was 6. The top vapour temperature was about 128° C. and the bottom temperature 152° C.

The different streams were analysed for the free acid content and the different components like, lactic acid, lactide(s), and lactic acid species. The term lactic acid species refers to the linear dimer and higher oligomers of lactic acid as well as (volatile) by-products formed during the depolymerisation of low molecular weight polylactic acid. Due to the volatility of the latter by-products, these were concentrated in the top of the column.

As can been seen from the free acid content, a high molecular weight polylactic acid can not directly, without further purification, be obtained from the bottom product stream of the distillation.

|  |  | Feed stream | Bottom stream |
|---|---|---|---|
| Lactic acid | wt. % | 2.6 | 0 |
| Meso-lactide | wt. % | 10.4 | 3.0 |
| L-lactide (incl. D-lactide | wt. % | 85.7 | 96.4 |
| Lactic acid species | wt. % | 1.3 | 0.6 |
| Free acid | meq/kg | 315 | 37 |
| Flow | kg/h | 67 | 54 |

EXAMPLE 6

Continuous Distillation of Rectified Lactide with Vapour Side Stream 65 kg/h rectified lactide was continuously purified in a distillation column having a top stream, a liquid bottom stream and a vapour side stream. In the top stream lactic acid and volatile lactic acid species were concentrated, in the bottom stream lactide and oligomers of lactic acid were concentrated. The vapour side stream contained lactide that is almost free of lactic acid and oligomers of lactic acid and could directly, without further purification, be polymerised to high molecular weight polylactic acid. The distillation column was packed with structured packing material in order to enhance contact between the vapour and the liquid and to minimize the liquid hold-up. The reflux ratio applied was 4. The top pressure was 25 mbara and the top vapour temperature about 127° C. The bottom temperature was about 144° C.

The different streams were analysed for the free acid content and the different components such as lactic acid, lactide (s), and lactic acid species. The term lactic acid species refers to the linear dimer and higher oligomers of lactic acid and (volatile) by-products formed during the depolymerisation of low molecular weight polylactic acid. Due to the volatility of the latter by-products, these were concentrated in the top of the column.

|  |  | Feed stream | Bottom stream | Vapour side stream | Top stream |
|---|---|---|---|---|---|
| Lactic acid | wt. % | 1.8 | 0 | 0 | 8.6 |
| Meso-lactide | wt. % | 13.7 | 5.6 | 7.9 | 41.8 |

|  |  | Feed stream | Bottom stream | Vapour side stream | Top stream |
|---|---|---|---|---|---|
| L-lactide (incl. D-Lactide) | wt. % | 83.6 | 93.1 | 91.6 | 44.9 |
| Lactic acid species | wt. % | 0.9 | 1.3 | 0.6 | 4.7 |
| Free acid | meq/kg | 337 | 157 | 19 | 1428 |

The lactide of the vapour side stream was polymerised to high molecular weight polylactic acid. Some properties of the produced polymer are given in the table below.

| Mn | g/mol | 101,200 |
|---|---|---|
| Mw | g/mol | 189,400 |
| MWD | — | 1.87 |

EXAMPLE 7

Continuous Distillation of Rectified Lactide with Vapour Side Stream 67 kg/h rectified lactide was continuously purified in a distillation column having a top stream, a liquid bottom stream and a vapour side stream. In the top stream lactic acid and volatile lactic acid species were concentrated, in the bottom stream lactide and oligomers of lactic acid were concentrated. The vapour side stream contained lactide that was substantially free of lactic acid and oligomers of lactic acid and could directly, without further purification, be polymerised to high molecular weight polylactic acid. The distillation column was packed with structured packing material in order to enhance contact between the vapour and the liquid and to minimise the liquid hold-up. The reflux ratio applied was 4. The top pressure was 25 mbara and the top vapour temperature about 127° C. The bottom temperature was about 146° C.

The different streams were analysed for the free acid content and the different components such as lactic acid, lactide (s), and lactic acid species. The term lactic acid species refers to the linear dimer and higher oligomers of lactic acid and (volatile) by-products formed during the depolymerisation of low molecular weight polylactic acid. Due to the volatility of the latter by-products, these were concentrated in the top of the column.

|  |  | Feed stream | Bottom stream | Vapour side stream | Top stream |
|---|---|---|---|---|---|
| Lactic acid | wt. % | 3.1 | 0 | 0 | 11.7 |
| Meso-Lactide | wt. % | 12.6 | 4.3 | 5.6 | 31.4 |
| L-lactide (incl. D-Lactide) | wt. % | 83.6 | 93.4 | 94.4 | 54.8 |
| Lactic acid species | wt. % | 0.8 | 2.3 | 0.6 | 2.2 |
| Free acid | meq/kg | 401 | 126 | 9.9 | 2020 |

The lactide of the side vapour stream is polymerised to high molecular weight polylactic acid. Some properties of the produced polymer are given in the table below. The molecular weight of the polylactic acid is determined by GPC in comparison with polystyrene standard.

| Mn | g/mol | 107,600 |
|---|---|---|
| Mw | g/mol | 196,800 |
| MWD | — | 1.83 |

EXAMPLE 8

Continuous Distillation of Rectified Lactide with Vapour Side Stream 67 kg/h rectified lactide was continuously purified in a distillation column having a top stream, a liquid bottom stream and a vapour side stream. In the top stream lactic acid and volatile lactic acid species were concentrated, in the bottom stream lactide and oligomers of lactic acid were concentrated. The vapour side stream contained lactide that was substantially free of lactic acid and oligomers of lactic acid and could be polymerised to high molecular weight polylactic acid. The distillation column was packed with structured packing material in order to enhance contact between the vapour and the liquid and to minimise the liquid hold-up. The reflux ratio applied was 6. The top pressure was 25 mbara and the top vapour temperature about 126° C. The bottom temperature was about 153° C.

The different streams were analysed for the free acid content and the different components such as lactic acid, lactide (s), and lactic acid species. The term lactic acid species refers to the linear dimer and higher oligomers of lactic acid and (volatile) by-products formed during the depolymerisation of low molecular weight polylactic acid. Due to the volatility of the latter by-products, these were concentrated in the top of the column.

|  |  | Feed stream | Bottom stream | Vapour side stream | Top stream |
|---|---|---|---|---|---|
| Lactic acid | wt. % | 2.2 | 0 | 0 | 9.0 |
| Meso-Lactide | wt. % | 18.8 | 4.9 | 8.2 | 61.8 |
| L-lactide (incl. D-Lactide) | wt. % | 76.7 | 92.0 | 91.0 | 21.5 |
| Lactic acid species | wt. % | 2.4 | 3.1 | 0 | 7.7 |
| Free acid | meq/kg | 419 | 239 | 15.7 | 2135 |

The lactide of the side vapour stream was polymerised to high molecular weight polylactic acid. Some properties of the produced polymer are given in the table below. The molecular weight of the polylactic acid is determined by GPC in comparison with polystyrene standard.

| Mn | g/mol | 92,400 |
|---|---|---|
| Mw | g/mol | 170,800 |
| MWD | — | 1.85 |

EXAMPLE 9

Continuous Distillation of Rectified Lactide with Vapour Side Stream 65 kg/h rectified lactide was continuously purified in a distillation column having a top stream, a liquid bottom stream and a vapour side stream. In the top stream lactic acid and volatile lactic acid species were concentrated, in the bottom stream lactide and oligomers of lactic acid were concentrated. The vapour side stream contained lactide that was substantially free of lactic acid and linear lactic acid oligomers and could directly, without further purification, be polymerised to high molecular weight polylactic acid. The distillation column was packed with structured packing material in order to enhance contact between the vapour and the liquid and to minimise the liquid hold-up. The reflux ratio applied was 6. The top pressure was 25 mbara and the top vapour temperature about 128° C. The bottom temperature was about 153° C.

The different streams were analysed for the free acid content and the different components such as lactic acid, lactide (s), and lactic acid species. The term lactic acid species refers to the linear dimer and higher oligomers of lactic acid and (volatile) by-products formed during the depolymerisation of low molecular weight polylactic acid. Due to the volatility of the latter by-products, these were concentrated in the top of the column.

|  |  | Feed stream | Bottom stream | Vapour side stream |
|---|---|---|---|---|
| Lactic acid | wt. % | 2.1 | 0 | 0 |
| Meso-Lactide | wt. % | 11.6 | 2.9 | 3.7 |
| L-lactide (incl. D-Lactide) | wt. % | 83.0 | 94.8 | 96.1 |
| Lactic acid species | wt. % | 2.3 | 2.4 | 0.2 |
| Free acid | meq/kg | 382 | 145 | 13.2 |

EXAMPLE 10

Acid Scavenging

Lactide with an acid content of 83 meq/kg was purified with an acid scavenging material. The acid scavenging material used was a powder of a glycidylmethacrylate based resin. The scavenging process was carried out at 130° C. with 5 wt. % of scavenging material. After 30 minutes the acid content had decreased to 40 meq/kg and after 90 minutes to 11 meq/kg. Such acid level is low enough in order to obtain high molecular weight polylactic acid.

EXAMPLE 11

Acid Scavenging

Lactide produced according to example 4 and 6 was further purified by re-circulating the lactide through a fixed bed filled with acid scavenging material. The acid scavenging material used was a powder of a glycidylmethacrylate based resin. The starting material was 600 kg lactide with a free acid content of 16.0 meq/kg. The amount of acid scavenging material used was 5 kg (0.8 wt. %). The temperature of the batch-wise scavenging process was kept around 120° C. After 2 hours the acid content was reduced to 13.7 meq/kg. After the packed bed, the free acid content of the lactide was found to be 2.5 meq/kg.

The invention claimed is:

1. A process for the purification of lactide from a crude lactide vapour product stream comprising at least said lactide, lactic acid, water and linear lactic acid oligomers, said crude lactide vapour product stream being produced by depolymerisation of low molecular weight polylactic acid in a reactor, which process comprises the steps of:
(a) feeding said vapour product stream to a rectification column having a feed inlet at the lower end of the column and an overhead vapour outlet at the upper end of the column, through the said feed inlet, said column being mounted onto the reactor such that components from the vapour product stream liquefying within the column are allowed to flow back into the reactor;
(b) establishing at the upper end of the column a first overhead vapour fraction consisting essentially of water, lactic acid and lactide, and at the lower end of the column a high-boiling fraction consisting essentially of lactide and higher-boiling linear lactic acid oligomers;
(c) condensing from said first overhead vapour fraction by means of a condenser at least the lactide to obtain a first liquid lactide containing condensate fraction;
(d) removing the first liquid lactide containing condensate fraction.

2. A process according to claim 1, wherein step (c) comprises partially condensing said first overhead vapour fraction, such that at least the water is left in the vapour phase and removed from the condenser.

3. A process according to claim 1, wherein step (c) comprises partially condensing said first overhead vapour fraction, such that at least the water and a major amount of the lactic acid are left in the vapour phase and removed from the condenser.

4. A process according to claim 1, wherein said first liquid lactide containing condensate fraction comprises at least 90 wt. % lactide and 0-10 wt. % lactic acid, preferably at least 96 wt. % lactide and 0-4 wt. % lactic acid.

5. A process according to claim 1, wherein the first liquid lactide containing condensate fraction of step (d) is subjected to one or more distillation steps.

6. A process according to claim 5, wherein said one or more distillation steps comprise the steps of:
(i) feeding the first liquid lactide containing condensate fraction into a distillation column, the column having a bottom end and a top end and a feed inlet between said bottom end and top end, the column further comprising a second overhead vapour outlet at the top end of the column, a liquid outlet at the bottom end and a vapour side outlet located between the feed inlet and the liquid outlet;
(ii) establishing
a second overhead vapour fraction comprising lactic acid in the top end of the column,
a bottom vapour fraction comprising lactide in the bottom end of the column, and
a bottom liquid fraction below the bottom vapour fraction comprising lactide and linear lactic acid oligomers;
(iii) removing second overhead vapour fraction through the overhead vapour outlet;
(iv) removing bottom vapour fraction through the vapour side outlet;
(v) removing bottom liquid fraction at the liquid outlet.

7. A process according to claim 6, further comprising the step of (vi) condensing the bottom vapour fraction comprising lactide obtained in step (iv) to obtain a second lactide containing condensate fraction.

8. A process according to claim 6, wherein the bottom vapour fraction and/or the second lactide containing condensate comprise at least 99 wt. %, preferably at least 99.5 wt. %, lactide.

9. A process according to claim 6, wherein the bottom liquid fraction is recycled to the reactor.

10. A process according to claim 1, said process further comprising the step of removing carboxylic acid and/or hydroxyl containing compounds in any of the lactide comprising fractions obtained in step (d).

11. A process according to claim 10, wherein said removing carboxylic acid and/or hydroxyl containing compounds in the lactide fraction obtained in step (d) comprises the steps of:
   I. contacting any of the lactide comprising fractions obtained in step (d) with a solid scavenger material comprising at least one functional moiety capable of forming a covalent bond with one or more carboxylic acid and/or hydroxyl containing compounds optionally present in said lactide comprising fraction, thereby allowing the at least one functional moiety of the scavenger material to selectively react with the one or more carboxylic acid and/or hydroxyl containing compounds optionally present in said lactide comprising fraction to form a covalent bond therewith;
   II. separating the scavenger material with bound carboxylic acid and/or hydroxyl containing compounds from the lactide comprising fraction to obtain a substantially purified lactide comprising fraction.

12. A process according to claim 11, wherein the at least one functional moiety of the solid scavenger material is selected from the group, consisting of epoxy, amine, amide, cyano and anhydride moieties.

13. A process according to claim 1, that is conducted in a continuous manner.

14. A process according to claim 1, that is conducted under reduced pressure.

15. A process according to claim 1, that is conducted under pressures in the range of 10-100 mbar.

16. A process according to claim 6, said process further comprising the step of removing carboxylic acid and/or hydroxyl containing compounds in any of the lactide comprising fractions obtained in step (iv) or (v).

17. A process according to claim 7, said process further comprising the step of removing carboxylic acid and/or hydroxyl containing compounds in any of the lactide comprising fractions obtained in step (vi).

18. A process according to claim 16, wherein said removing carboxylic acid and/or hydroxyl containing compounds in the lactide fraction obtain in step (iv) or (v) comprises the steps of:
   I. contacting any of the lactide comprising fractions obtained in step (iv) or (v) with a solid scavenger material comprising at least one functional moiety capable of forming a covalent bond with one or more carboxylic acid and/or hydroxyl containing compounds optionally present in said lactide comprising fraction, thereby allowing the at least one functional moiety of the scavenger material to selectively react with the one or more carboxylic acid and/or hydroxyl containing compounds optionally present in said lactide comprising fraction to form a covalent bond therewith;
   II. separating the scavenger material with bound carboxylic acid and/or hydroxyl containing compounds from the lactide comprising fraction to obtain a substantially purified lactide comprising fraction.

19. A process according to claim 17, wherein said removing carboxylic acid and/or hydroxyl containing compounds in the lactide fraction obtained in step (vi) comprises the steps of:
   I. contacting any of the lactide comprising fractions obtained in step (vi) with a solid scavenger material comprising at least one functional moiety capable of forming a covalent bond with one or more carboxylic acid and/or hydroxyl containing compounds optionally present in said lactide comprising fraction, thereby allowing the at least one functional moiety of the scavenger material to selectively react with the one or more carboxylic acid and/or hydroxyl containing compounds optionally present in said lactide comprising fraction to form a covalent bond therewith;
   II. separating the scavenger material with bound carboxylic acid and/or hydroxyl containing compounds from the lactide comprising fraction to obtain a substantially purified lactide comprising fraction.

20. A process according to claim 18, wherein the at least one functional moiety of the solid scavenger material is selected from the group, consisting of epoxy, amine, amide, cyano and anhydride moieties.

21. A process according to claim 19, wherein the at least one functional moiety of the solid scavenger material is selected from the group, consisting of epoxy, amine, amide, cyano and anhydride moieties.

* * * * *